(12) United States Patent
Sanders et al.

(10) Patent No.: US 7,722,625 B2
(45) Date of Patent: May 25, 2010

(54) MODULAR BONE CLAMP INSTRUMENT

(75) Inventors: Roy W. Sanders, Tampa, FL (US);
Kristen A. Salzgeber, Parma, OH (US);
Jessica M. Williams, South Lyon, MI
(US); Kyle D. Blatt, Pickerington, OH
(US); Christopher K. Bremer, Warsaw,
IN (US); Rebecca D. Oberst, North
Webster, IN (US)

(73) Assignee: DePuy Products, Inc., Warsaw, IN (US)

( * ) Notice: Subject to any disclaimer, the term of this patent is extended or adjusted under 35 U.S.C. 154(b) by 1318 days.

(21) Appl. No.: 10/881,803

(22) Filed: Jun. 30, 2004

(65) Prior Publication Data

US 2006/0004379 A1 Jan. 5, 2006

(51) Int. Cl.
*A61B 17/66* (2006.01)
(52) U.S. Cl. .................................... 606/105
(58) Field of Classification Search ................. 606/54, 606/57, 58, 72, 86, 105, 205, 207, 208, 74, 606/324, 99, 300, 86 R; 433/153, 159; D8/52
See application file for complete search history.

(56) References Cited

U.S. PATENT DOCUMENTS

| | | | | |
|---|---|---|---|---|
| 1,985,108 | A | * | 12/1934 | Rush .......................... 606/86 R |
| 3,604,414 | A | * | 9/1971 | Borges ........................ 606/105 |
| 3,783,873 | A | | 1/1974 | Jacobs |
| 4,706,660 | A | | 11/1987 | Petersen |
| 5,129,907 | A | | 7/1992 | Heldreth et al. |
| 5,284,482 | A | | 2/1994 | Mikhail |
| 5,342,364 | A | | 8/1994 | Mikhail |
| 5,370,646 | A | * | 12/1994 | Reese et al. .................. 606/324 |
| 5,575,793 | A | | 11/1996 | Carls et al. |
| 5,658,291 | A | | 8/1997 | Techiera |
| 5,716,360 | A | | 2/1998 | Baldwin et al. |
| 5,741,252 | A | | 4/1998 | Mazzio et al. |
| 5,951,564 | A | | 9/1999 | Schroder et al. |
| 5,968,051 | A | | 10/1999 | Luckman |
| 6,010,509 | A | | 1/2000 | Delgado et al. |
| 6,077,271 | A | | 6/2000 | Huebner et al. |
| 6,080,162 | A | | 6/2000 | Dye et al. |
| 6,315,780 | B1 | | 11/2001 | Lalonde |
| 6,589,241 | B1 | | 7/2003 | Townsend et al. |

FOREIGN PATENT DOCUMENTS

| | | |
|---|---|---|
| EP | 0 393 151 B1 | 2/1989 |
| EP | 0 891 159 B1 | 8/2003 |
| WO | WO 89/06939 | 2/1989 |

* cited by examiner

*Primary Examiner*—Eduardo C Robert
*Assistant Examiner*—David Comstock
(74) *Attorney, Agent, or Firm*—Maginot, Moore & Beck

(57) ABSTRACT

A modular bone clamp instrument includes a first elongated arm with a first clamping surface and a second elongated arm with a second clamping surface. A ratchet mechanism is provided between the first elongated arm and the second elongated arm. The ratchet mechanism allows the first elongated arm to move in a first direction, but prevents movement of the first elongated arm in an opposite direction. A squeeze handle is connected to the second elongated arm. The squeeze handle includes a forward handle member and a rear handle member. The rear handle member includes a head with an open chamber. The second elongated arm includes a shoulder that fits in the open chamber. A retention pin extends through the head and shoulder to secure the handle to the second elongated arm. Rotation of the retention pin allows the handle to be released from the second elongated arm.

25 Claims, 7 Drawing Sheets

MODULAR BONE CLAMP INSTRUMENT

BACKGROUND

Bone clamps are well known in the medical profession for use in repairing broken and fractured bones. A severely broken bone typically requires attachment of a periosteum compression plate (or "peri-plate") to the bone. The peri-plate bridges the fracture and provides stability for the bone either permanently or temporarily as the break in the bone heals. Bone clamps are used to hold the peri-plate in position when it is attached to the bone. In particular, once a broken bone is set by a physician, a peri-plate is positioned against the bone in a desirable location that spans across the break. One or more bone clamps are then introduced to compress the peri-plate against the bone and hold the peri-plate to the desired location on the bone. With the peri-plate fixed in place against the bone, the physician uses screws or other attachment means to secure the peri-plate to the bone. The bone clamps are then removed from the bone/plate interface, while the peri-plate remains secured to the bone and provides stability to the bone as it heals.

Bone clamps typically comprise a forceps-like instrument having a squeeze handle and opposed jaws that provide two opposed clamping surfaces positioned on opposing jaws. A ratchet or other mechanism is used to permit movement of the opposed clamping surfaces toward each other, but prevent movement of the opposed clamping surfaces away from each other. This allows the user of a bone clamp to clamp the peri-plate to the bone during a surgical procedure without having to continually squeeze the handle. After the need for clamping the peri-plate to the bone is past, the ratchet mechanism is released and the two opposed clamping surfaces move away from each other, thereby removing the clamp upon the peri-plate and bone.

Several problems are present with existing bone clamps. First, bone clamps typically include a single jaw size and associated clamping surface for use with numerous shapes and sizes of bones. For example, a surgeon may have only a single bone clamp for use in association with the tibia, femur, humerus, and radius/ulna. With only a single jaw size for various bones, the clamping surface provided by the jaw is often an inadequate fit for the bone in question. Such an inadequate fit may allow the bone clamp to improperly move and drift around the bone/plate interface during operation. Accordingly, it would be desirable to provide a bone clamp with numerous jaws of different shapes and sizes that could be used in association with the bone clamp.

Another problem with current bone clamps is that the weight of the bone clamp creates a significant torque around the bone when the bone clamp is in place. This torque is undesirable, as it may cause the plate to move or shift once it is strategically placed upon the bone. Furthermore, this undesirable torque may even cause the fractured bone to shift once it is set. Therefore, it would be desirable to provide a bone clamp with reduced weight or a method for removing weight from the bone clamp when in use, thereby reducing the torque exerted on the bone during surgical procedures.

Yet another problem with current bone clamp instruments is that the handle of the instrument protrudes from the surgical site during use and invades the surgeon's operating space. This is problematic for the surgeon, as the surgeon needs to be able to clearly view the surgical site to ensure proper alignment of the bone/plate interface. The surgeon also needs adequate space to use other instrumentation in order to drill screws when securing the peri-plate to the bone. Handling of this instrumentation is often awkward and difficult, but it becomes even more awkward and difficult if one or more handles from the bone clamp are protruding from the surgical site. Therefore, it would be desirable to provide a bone clamp with a handle that may be removed once the clamp is in position upon the bone and peri-plate.

Accordingly, it would be desirable to provide a bone clamp which overcomes one or more of the above-mentioned drawbacks. In particular, it would be desirable to provide a bone clamp with interchangeable jaws each being designed and dimensioned for use with different bones. It would also be desirable to provide a bone clamp with a removable handle.

SUMMARY

A bone clamp that includes one or more of the above-mentioned desirable features comprises a first elongated arm, a second elongated arm and a handle. The first elongated arm includes an elongated portion positioned between a proximal end and a distal end. A first clamp member is connected to the distal end of the first elongated arm. The second elongated arm also includes an elongated portion positioned between a proximal end and a distal end. A second clamp member is provided on a jaw formed on the distal end of the second elongated arm. The second elongated arm is arranged substantially parallel to the first elongated arm. Runners on the first elongated arm are positioned in tracks formed in a channel on the second elongated arm.

A squeeze handle is attached to the second elongated arm. The squeeze handle comprises a forward handle member pivotably connected to a rear handle member. Rotational movement of the forward handle member toward the rear handle member causes a tail on the forward handle member to forcibly engage the proximal end of the first elongated arm. When the tail on the forward handle member forcibly engages the first elongated arm, the first elongated arm moves relative to the second elongated arm in a first direction that causes the first clamp member to move toward the second clamp member. A ratchet is arranged and disposed upon the first elongated arm and the second elongated arm. The ratchet comprises teeth on the second elongated arm and a pawl positioned on the first elongated arm. Engagement of the pawl with the teeth permits motion of the first elongated arm relative to the second elongated arm in the first direction, but prevents motion of the first elongated arm relative to the second elongated arm in an opposite direction. A release lever is provided on the first elongated arm in contact with the pawl. Rotation of the release lever causes the pawl to disengage the teeth, thereby allowing movement of the first arm relative to the second arm in the opposite direction such that the first clamp member moves away from the second clamp member.

The rear handle member is removeably connected to the proximal end of the second elongated arm. In particular, the proximal end of the second elongated arm includes a shoulder arranged and disposed in a head of the rear handle member. A release pin having a locking shaft extends through the head of the rear handle member and the shoulder of the second elongated arm. Rotation of the release pin allows the shoulder of the second elongated arm to be released from the head of the rear handle member.

DESCRIPTION

Figure 1:
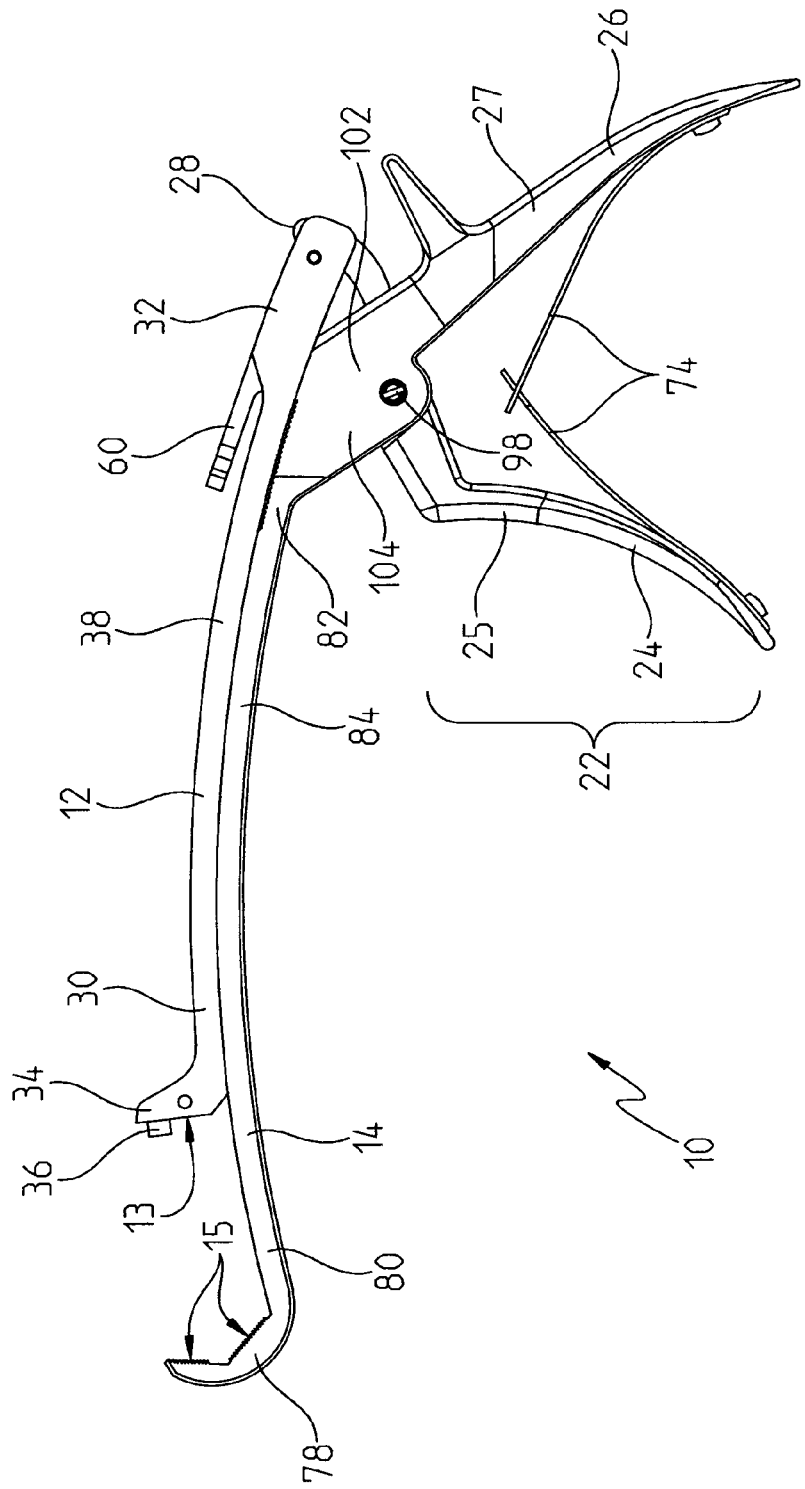
FIG. 1 shows an elevational side view of a modular bone clamp instrument that incorporates the features of the present invention.

With reference to FIG. 1, a modular bone clamp instrument 10 comprises a superior/top arm 12 having a first clamping surface 13 and an inferior/bottom arm 14 having a second clamping surface 15. The top arm 12 and bottom arm 14 are slightly curved and are substantially parallel to each other, such that the curved portions of each arm are generally concentric. The first clamping surface 13 of the top arm 12 is substantially opposed to the second clamping surface 15 of the bottom arm 14. A ratchet mechanism is provided between the top arm 12 and the bottom arm 14 to retain the position of the arms relative to one another during clamping. A squeeze handle 22 is releasably connected to the top arm 12 and bottom arm 14. The squeeze handle includes a forward/finger handle 24 and a rear/thumb handle 26. Movement of the forward handle 24 toward the rear handle 26 causes the first clamping surface 13 to move toward the second clamping surface 15. The modular bone clamp instrument is generally comprised of a metallic material, such a stainless steel. This provides a clamp having a solid structure capable of exerting significant force without deforming the clamp. This also allows the parts of the clamp to be easily cleaned and sterilized. Of course, other materials may be used for the clamp without departing from the spirit and scope of the invention.

Figure 2:
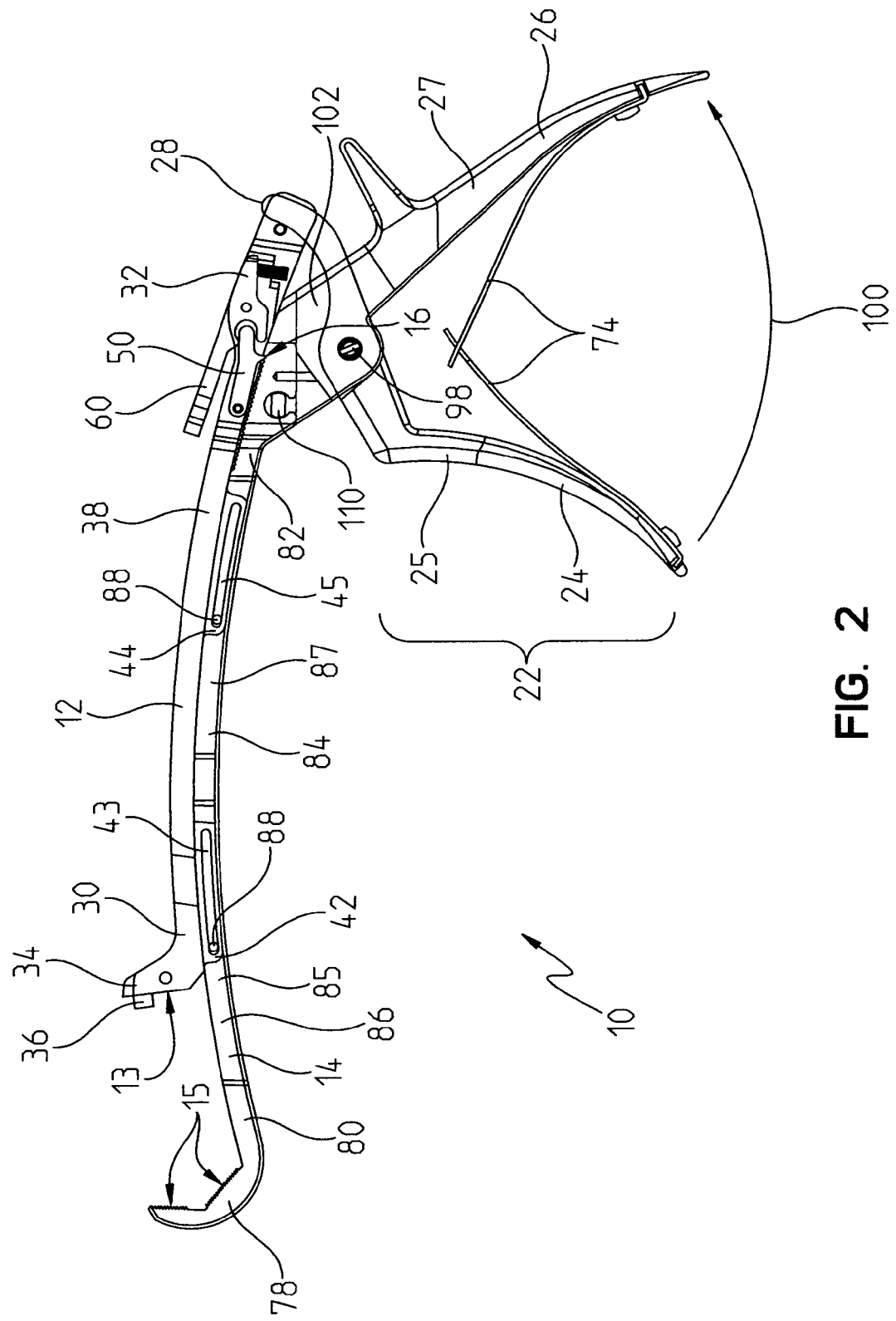
FIG. 2 shows a side cutaway elevational view of the modular bone clamp instrument of FIG. 1.

With reference to FIG. 2, the top arm 12 comprises an elongated portion 38 positioned between a distal end 30 and a proximal end 32. The first clamping surface 13 is located on the distal end 30 of the top arm 12, and is provided along a finger 34 on the distal end of the top arm. The finger 34 extends substantially perpendicular to the elongated portion 38 of the top arm. A tab 36 is provided on the finger 34 and the tab extends from first clamping surface 13. As discussed in further detail below, the tab 36 is designed to engage one of a plurality of recesses on a periosteum (or "peri") compression plate. The first clamping surface 13 is generally smooth, but in alternative embodiments a textured surface may be desirable for providing greater surface friction.

The elongated portion 38 of the top arm 12 is generally arcuate in shape with a rectangular cross-section. Two runners 42 and 44 extend downward away from the bottom of the elongated portion 38. A first runner 42 is positioned near the distal end 30 of the top arm and a second runner 44 is positioned near the middle portion of the top arm. The first runner 42 and second runner 44 are both elongated and both include a guide hole 43, 45 that extends along the length of the runner.

Figure 3:
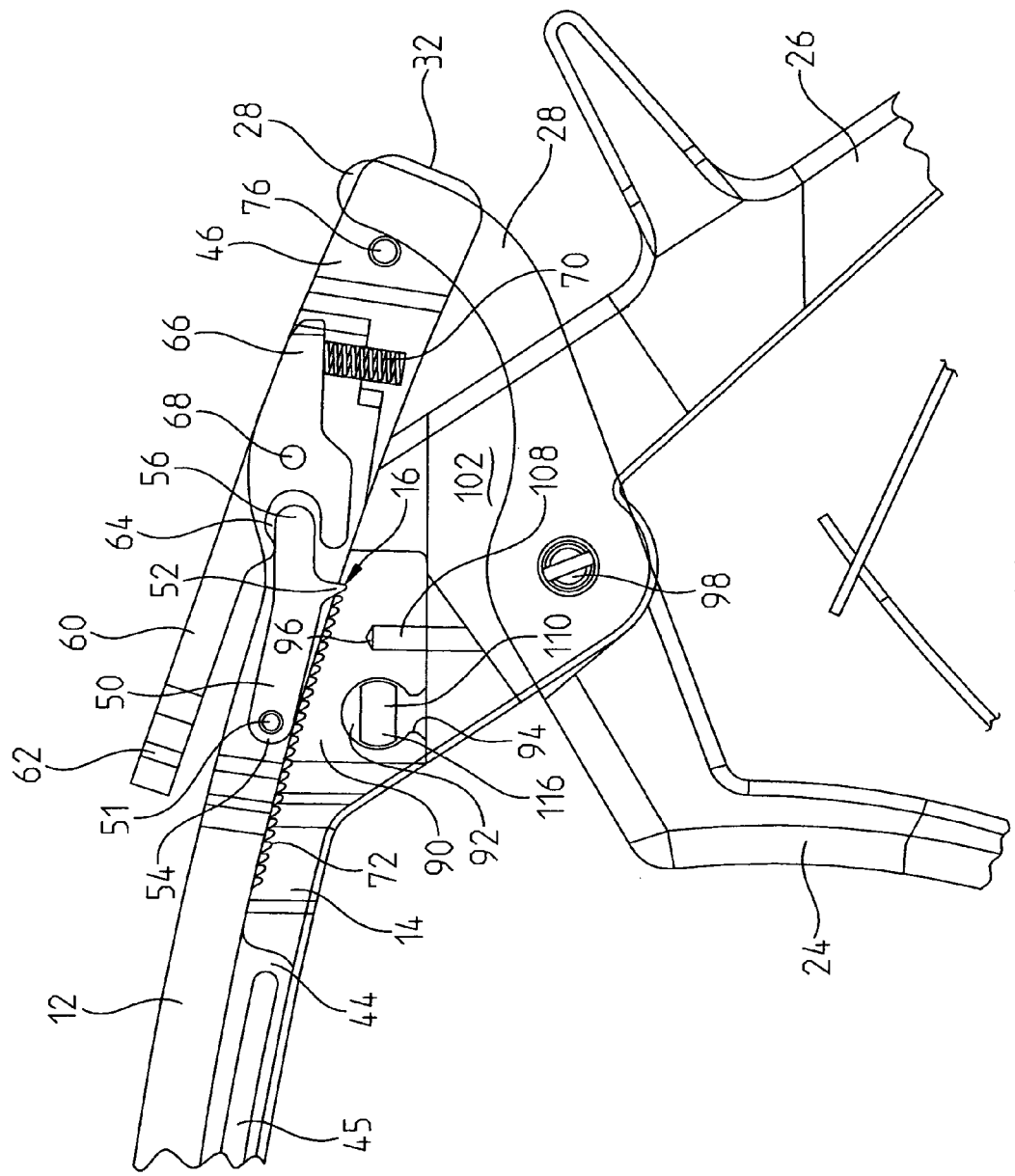
FIG. 3 shows a fragmentary enlarged view of the modular bone clamp instrument of FIG. 1 near a proximal end of a top arm and a proximal end of a bottom arm.

As shown in FIG. 3, the proximal end 32 of the top arm includes a hollow flared portion 46 that houses several components designed to assist with or restrict movement of the top arm relative to the bottom arm. In particular, a pawl 50 of the ratchet 16 is pivotably retained in the top arm 12 near the flared portion 46. A pin 51 fastened to the top arm 12 extends through a hole in the pivot end 54 of the pawl 50 and secures the pawl to the top arm while allowing the pawl to pivot up and down within the top arm. The pawl 50 includes a tip 52 and an adjacent tongue 56 located opposite the pivot end 54 of the pawl. The tip 52 is designed to engage teeth 72 on the ratchet 16 in order to prevent backward movement of the top arm which would allow the first clamping surface 13 to move away from the second clamping surface 15.

A release lever 60 is provided that engages the tongue 56 of the pawl 50. The release lever includes an enlarged finger pad 62 at one end, a spring pad 66 at an opposite end, and a fulcrum 68 positioned therebetween. The fulcrum is provided by a pin 68 fastened to the walls of the hollow flared portion 46 of the top arm 12. The pin 68 extends through a hole in the release lever and secures the release lever to the top arm while allowing the release lever to rotate about the fulcrum. A mouth 64 is provided on the release lever 60 near the fulcrum 68. The mouth 64 is arranged to receive the tongue 56 of the pawl and engage the tongue 56 when the release lever is rotated. In particular, when the finger pad 62 of the release lever 60 is rotated in an upward direction away from the top arm, the mouth 64 of the release lever forces the tongue 56 of the pawl 50 upward and releases the pawl tip 52 from engagement with the teeth 72. A spring 70 is disposed within the hollow flared portion 46 of the top arm 12. The spring 70 is in contact with the spring pad 66 on the release lever and biases the spring pad end of the release lever upward. This upward bias on the spring pad results in a downward bias on the finger pad 62. With the release lever biased in this manner, the mouth 64 of the release lever biases the pawl 50 downward to encourage engagement of the tip 52 of the pawl with the teeth 72.

With reference again to FIG. 2, the bottom arm 14 comprises an elongated portion 84 positioned between a distal end 80 and a proximal end 82. The second clamping surface 15 is located on the distal end 80 of the bottom arm 14, and is provided on a jaw 78 formed on the distal end of the bottom arm. The jaw 78 curves upward from the elongated portion of the bottom arm 15. The second clamping surface 15 is provided on the jaw substantially opposed to the first clamping surface 13 on the top arm. As shown in FIG. 2, the second clamping surface may include a plurality of offset surfaces that, in aggregate, provide a concave clamping surface. A concave clamping surface allows the second clamping surface to contact the bone at two or more locations during clamping, thereby adding stability to clamp. The second clamping surface is generally textured with a plurality of small tooth-like projections extending from the clamping surface. These projections are designed to grip the bone when the clamp is used. However, in alternative embodiments the second clamping surface may be smooth. In one embodiment, several bottom arms with jaws of differing sizes and shapes are provided with the modular bone clamp instrument. The different jaws provide different clamping surfaces appropriate for use with different types of bones.

The elongated portion 84 of the bottom arm 14 includes a channel 86 that provides a track for the first runner 42 and second runner of the top arm 12. The channel includes a first length of track 85 designed to receive the first runner 42 and a separate second length of track 87 designed to receive the second runner 44. Stationary pins 88 are positioned the first length 85 and the second length 87 of track and traverse the channel from side-to-side. The first runner 42 and second runner 44 are retained within the first length of track 85 and second length of track 87, respectively, by the stationary pins 88, which extend through the guide holes 43 and 45 of the first runner and second runner. With the stationary pins 88 extending through the guide holes 43 and 45 of the runners, the top arm 12 is operable to slide back and forth along the second arm 14 to the extent permitted by the guide holes 43 and 45. At the same time, the top arm 12 is slideably attached to the bottom arm 14, as the stationary pins 88 on the bottom arm 14 prevent the runners 42 and 44 and connected top arm 12 from separation from the bottom arm 14.

With reference again to FIG. 3, the proximal end 82 of the bottom arm 14 includes a plurality of teeth 72 arranged on the top surface. The teeth 72 are designed to engage the tip 52 of the pawl 50 and are generally sloped such that the teeth are slanted towards the distal end of the bottom arm. This orientation allows the pawl 50 to move in one direction but prevents movement in the opposite direction while the tip 52 of the pawl is in contact with the teeth 72. Together, the teeth 72 on the bottom arm 14 and the pawl 50 on the top arm 12 provide a ratchet mechanism 16 between the top arm and bottom arm.

Figure 6:
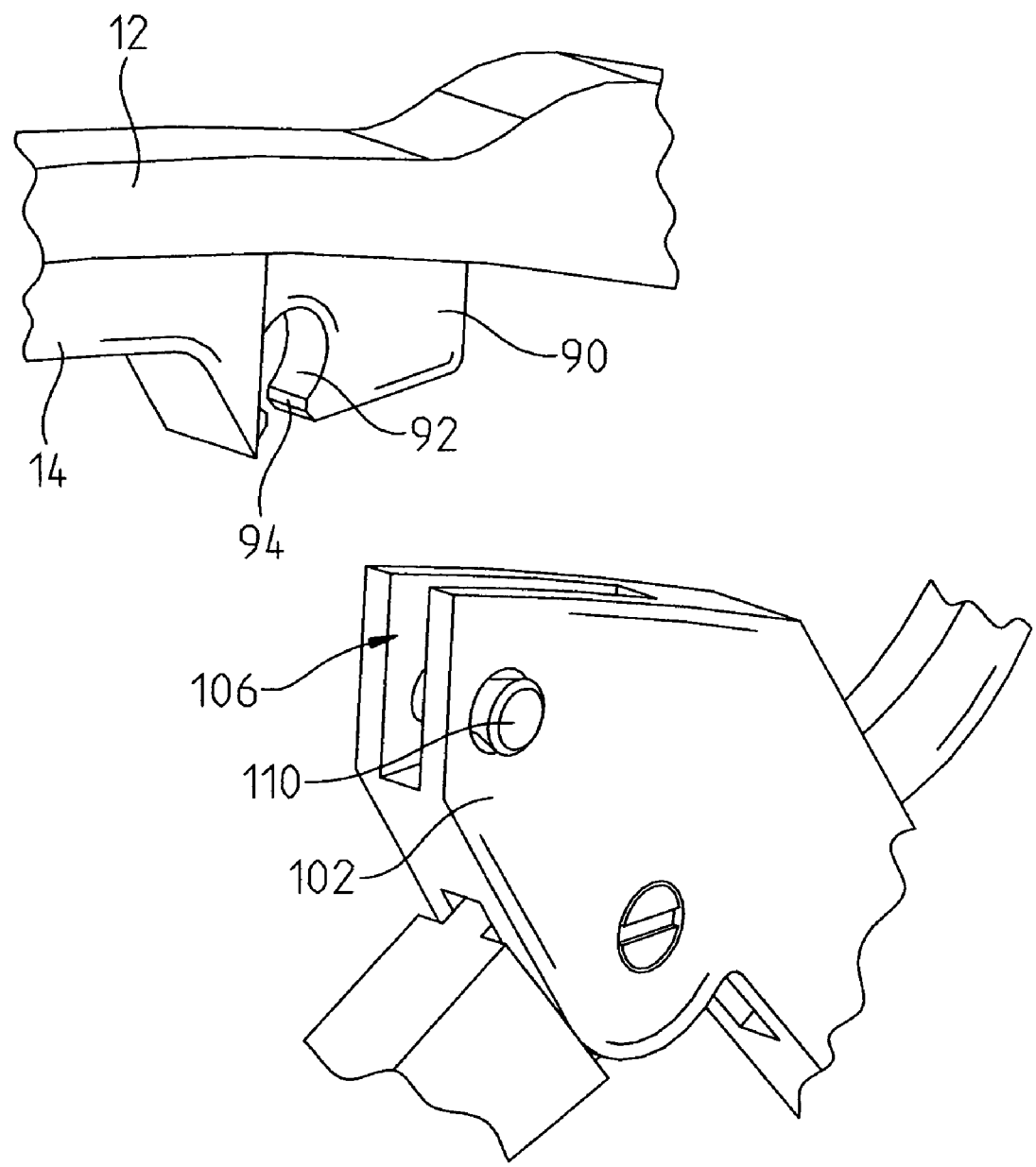
FIG. 6 shows an enlarged perspective view of the modular bone clamp instrument of FIG. 1 near the proximal end of the bottom arm with the handle released from the bottom arm.

As shown in FIGS. 3 and 6, the proximal end 82 of the bottom arm 14 also includes a shoulder 90. The height of the shoulder 90 is generally greater than the height of the elongated portion 84 of the bottom arm 14, but the width of the shoulder is generally less than that width of the elongated portion of the bottom arm. The shoulder 90 includes a circular cavity 92 that extends laterally through the shoulder. An opening 94 is provided at the bottom of the shoulder 90 that leads to the cavity 92. A bore 96 is also provided in the shoulder. As explained in further detail below, the cavity 92, opening 94, and bore 96, are used to releasably secure the handle 22 to the bottom arm 14.

The squeeze handle 22 includes a forward handle portion 24 and a rear handle portion 26 pivotably joined by a pivot pin 98. The rear handle portion 26 includes an enlarged head portion 102 connected to a thumb/palm post 27. The head portion 102 comprises two parallel faces 104 separated by an open chamber 106 (see FIG. 6). The open chamber is designed to receive the shoulder 90 of the second arm such that the shoulder 90 fits between the two parallel faces 104. A stability pin 108 is mounted to the head in the open chamber 106. The stability pin is designed and dimensioned to fit into the bore 96 on the shoulder 90 and assist in stabilizing the shoulder within the head 102.

Figure 4A:
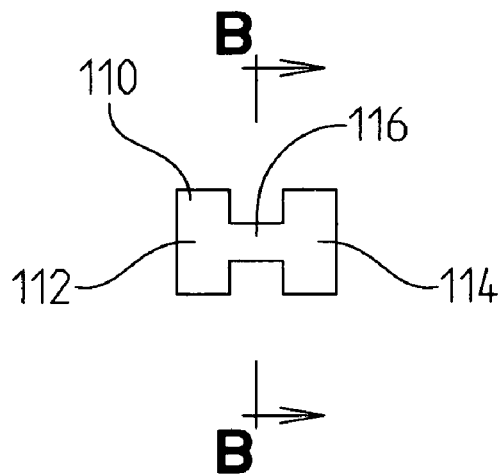
FIG. 4A shows a side elevational view of a release pin included on the modular bone clamp instrument of FIG. 1.
Figure 4B:
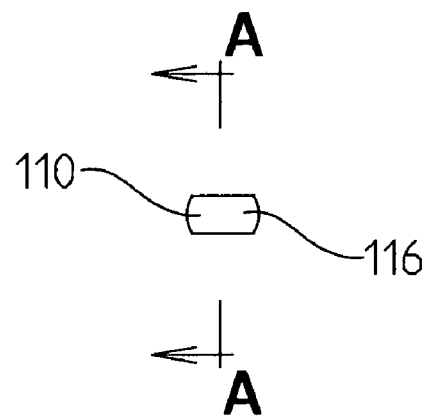
FIG. 4B shows a cross-sectional view of the release pin along line B-B of FIG. 4A.
Figure 4C:
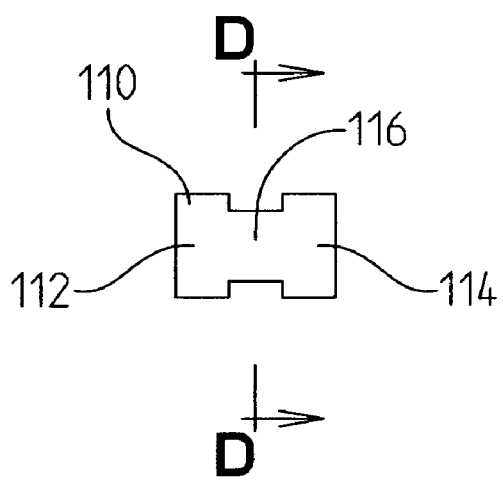
FIG. 4C shows a side elevational view of the release pin of FIG. 4A rotated ninety degrees.
Figure 4D:
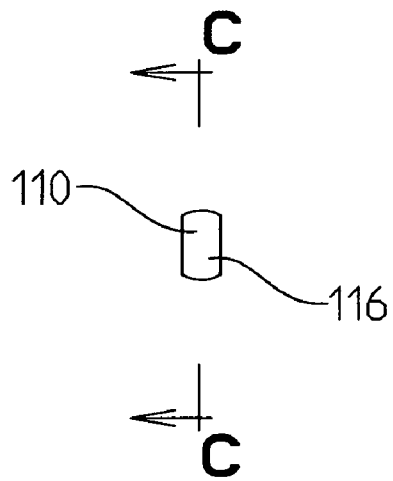
FIG. 4D shows a cross-sectional view of the release pin along line D-D of FIG. 4C.
Figure 5:
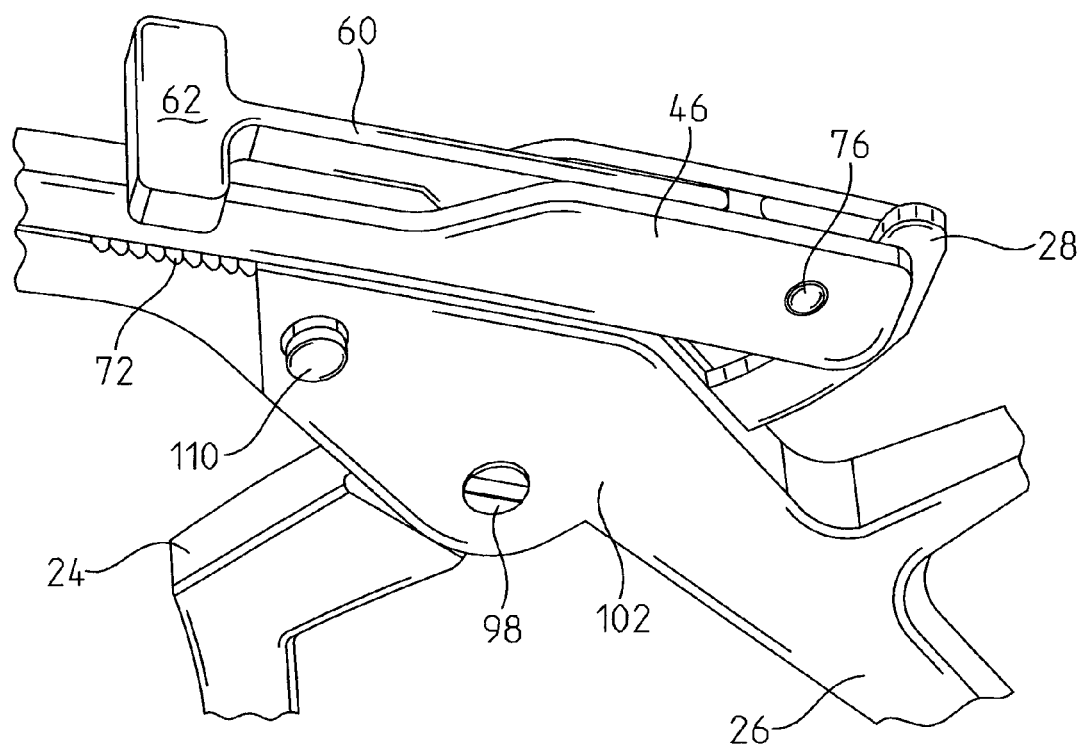
FIG. 5 shows an enlarged perspective view of the modular bone clamp instrument of FIG. 1 near the proximal end of the top arm and the proximal end of the bottom arm.

A release pin 110 is rotatably retained in a hole of the head 102. As shown in FIG. 4A, the release pin 110 includes a first end plate 112 and a second end plate 114 with a locking shaft 116 arranged in between. As shown in FIG. 4B, the locking shaft is formed with a cross-sectional first diameter that is greater than a cross-sectional second diameter. The first diameter of the locking shaft 116 is greater than the diameter of the cavity opening 94 in the shoulder of the bottom arm. At the same time, the second diameter of the locking shaft 116 is less than the diameter of the cavity opening 94 in the shoulder of the bottom arm. A slot (not shown) is provided in the second end plate 114 to allow the tip of a screwdriver to turn the release pin 110 to expose either the first diameter or second diameter of the locking shaft 116 to the cavity opening 94. Referring again to FIG. 3, when the shoulder 90 of the second arm 14 is inserted into the head 102 of the rear handle, the release pin 110 extends through the cavity 92 in the shoulder, thereby securing the second arm 14 to the rear handle 26. In particular, when the second arm 14 is secured to the rear handle 26, the release pin 110 is in a first position such that the greater first diameter of the locking shaft 116 spans across the cavity opening 94. When the release pin 110 is in this position, the bottom arm can not be released from the rear handle. However, ninety degree rotation of the release pin 110 results in orientation of the locking shaft 116 in a second position such that the smaller second diameter of the locking shaft 116 is presented to the cavity opening 94. When the release pin 110 is in this position, the bottom arm 14 is free to release from the rear handle 26. Because the bottom arm 14 can be released from the handle 22, numerous interchangeable bottom arms are provided for use in association with the modular bone clamp instrument. Each bottom arm includes a second clamping surface 15 of a different size and shape for use in association with different bones.

The forward handle portion 24 of the handle 22 comprises a finger post 25 connected to a tail 28. The pivot pin 98 connects the first handle portion 24 to the second handle portion 26 and allows the forward handle portion 24 to pivot with respect to the rear handle portion 26. The proximal end 32 of the top arm 12 includes an opening, and the tail 28 of the forward handle portion 24 is dimensioned to fit into the opening in the proximal end 32 of the top arm 12. When situated in the proximal end 32 opening, the tail 28 abuts a cross pin 76 that is fixed to the top arm 12 and traverses laterally across the opening in the proximal end of the first arm. Movement of the forward handle portion 24 toward the rear handle portion 26 in the direction of arrow 100 (see FIG. 2) causes the forward handle portion to pivot and moves the tail 28 into forcible engagement with the cross pin 76. Two spring arms 74 are respectively connected to the forward handle portion 24 and the rear handle portion 26. Each spring arm 74 includes a first end that is secured to the handle 22 and a second end that contacts the opposing spring arm. The spring arms 74 bias the forward handle portion 24 away from the rear handle portion 26 such that the finger post 25 is removed from the palm post 27 when an outside force is not being applied to the handle 22.

In operation, the modular bone clamp is used during surgical procedures to repair broken or fractured bones. Before the surgical procedure begins, the surgeon (or surgical assistant) chooses one of several bottom arms with different sized and shaped jaws and associated clamping surfaces. The bottom arm chosen by the surgeon depends upon the bone to be repaired. The modular bone clamp is then constructed by inserting the runners 42 and 44 of the top arm 12 into the tracks 85 and 87 of the selected bottom arm 14. The handle 22 is then attached to the arms 12 and 14 by inserting the shoulder 90 of the second arm into the open chamber 106 of the head 102. In order to properly seat the shoulder 90 in the head 102, the release pin 110 must be properly oriented to allow the smaller second diameter of the release pin to pass through the opening 94 and into the cavity 92 of the shoulder. At the same time the stability pin 108 in the head is inserted into the bore 96 in the shoulder. Once the shoulder 90 is properly seated in the head 102, the release pin 110 is rotated ninety degrees to lock the bottom arm 14 to the rear handle 26.

Figure 7:
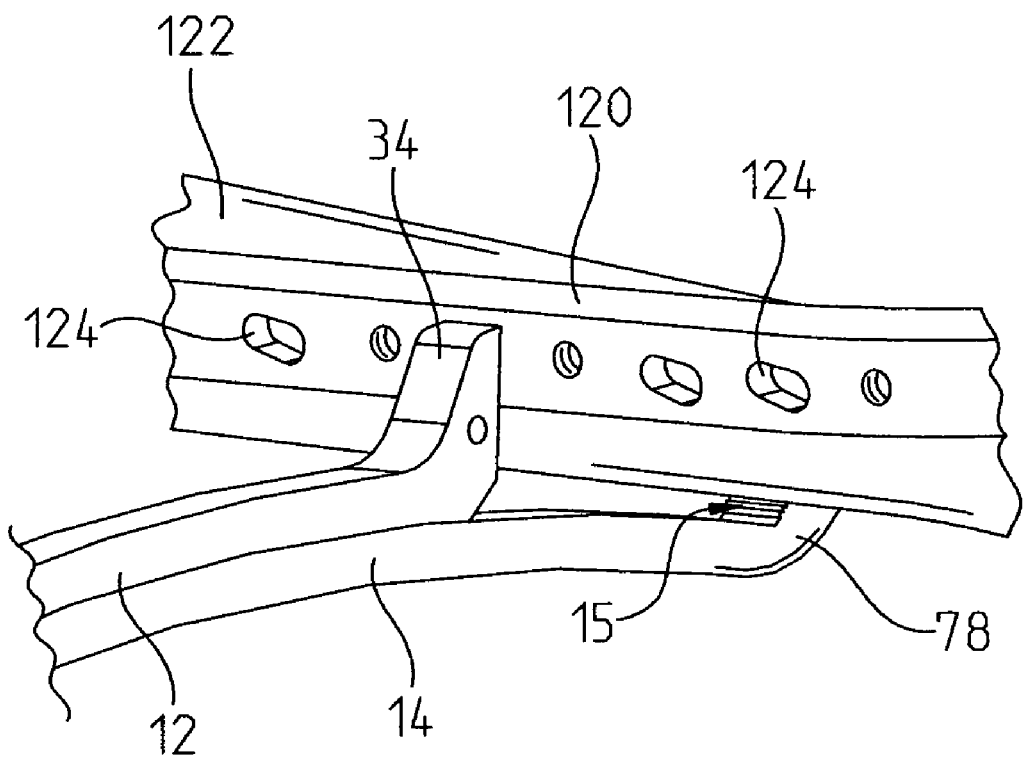
FIG. 7 shows an enlarged perspective view of a first clamp member and a second clamp member of the modular bone clamp of FIG. 1 compressing a peri-plate against a bone.

With the modular bone clamp constructed, the surgical procedure begins. Once the bone is exposed during surgery, a peri-plate 120 is positioned against the bone 122 in the area of the fracture or break, as illustrated in FIG. 7. Peri-plates 120 include a plurality of holes 124. Some of these holes are provided to assist the surgeon in retaining the peri-plate in place during a surgical procedure and other holes are provided for the purpose of fixing the peri-plate to the bone. With the peri-plate 120 positioned against the bone 122, the surgeon first wraps the jaw 78 of the bottom arm 14 around the bone such that the second clamping surface 15 contacts the bone on the opposite side from the peri-plate. The tab 36 on the first clamping surface 13 is then aligned with one of the holes 124 on the peri-plate designed to assist with holding the peri-plate in place during the surgical procedure. After this, the surgeon grips the handle 22 of the bone clamp 10 and moves the finger post 25 toward the palm post 27 in the direction of arrow 100 (see FIG. 2). When the finger post 25 is moved toward the palm post 27, the tail 28 of the forward handle is forced against the cross pin 76 on the top arm 12. As the surgeon continues to squeeze the handle 22, the tail 28 forces the top arm 12 to slide along the bottom arm 14, thereby moving the first clamping surface 13 toward the second clamping surface 15. Small incremental advancements of the top arm are captured by the ratchet 16, as the tip 52 of the pawl 50 engages successive teeth 72 on the bottom arm 14. The tip 52 of the pawl 50 remains in constant contact with the teeth 72 as the first clamping surface 13 is moved toward the second clamping surface 15 since the spring 70 on the release lever 60 biases the mouth 64 of the release lever 60 and the associated pawl 50 downward toward the teeth 72. During this action, the slanted teeth 72 allow the pawl 50 and the associated tip 52 to move forward, but prohibit backwards movement of the pawl and top arm 12. The surgeon continues to squeeze the handle 22 until the tab 36 of the top arm is fully inserted into the desired hole in the peri-plate, the first clamping surface is tightly pressed against the peri-plate, and the second clamping surface is tightly pressed against the bone.

With the peri-plate clamped to the bone, the surgeon may choose to remove the handle 22 from the top and bottom arms of the modular bone clamp instrument. In order to accomplish this, the release pin 110 is rotated ninety degrees to expose the smaller diameter of the locking shaft 116 to the opening 94 in the shoulder 90. With the locking shaft oriented in this way, the shoulder 90 of the bottom arm 14 is removed from the head 102 of the rear handle portion 26. Removal of the handle from the clamp conveniently removes a significant weight from the clamp and thereby reduces the amount of torque placed on the bone and/or bone/clamp interface. The reduction in force is especially significant because of both the weight of the handle and its relatively large distance from the axis of rotation that only contributes to the overall torque provided by the clamp. Furthermore, removal of the handle from the bone clamp frees a significant amount of additional operational space for the surgeon. This removes clutter from the operating space and makes the operational procedure easier for the surgeon. At the same time, removal of the handle 22 has no adverse effects on the strength of the clamp, as the first arm 12 and second arm 14 remain fixed in place by the ratchet 16 provided between the two arms. Thus, the modular bone clamp instrument provides a convenient device wherein the handle of the instrument can be removed while the clamp itself continues to secure the peri-plate to the bone.

After the surgeon attaches the peri-plate to the bone using screws or other attachment devices, the clamp is removed. This is easily accomplished by rotation of the release lever 60 which disengages the pawl 50 from the teeth 72 of the ratchet. In particular, when the surgeon desires to release the clamp on the peri-plate, he or she touches the underside of the finger pad 62 and rotates the end of the release lever 60 away from the top arm 12. Rotation of the release lever 60 causes the mouth 64 of the release lever to engage the tongue 56 of the pawl 50 and move the tip 52 of the pawl away from the teeth 72. Once the pawl 50 is disengaged from the teeth 72, the tension in the clamp is removed, and the first clamping surface 13 moves away from the second clamping surface 15.

The jaw 78 is then removed from the opposite side of the bone, and the modular bone clamp is removed from the work area where it is cleaned and prepared for subsequent surgical procedures.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A bone clamp operable to provide a clamping force on a bone and plate, the bone clamp comprising: a. a first elongated arm with a first clamping surface; b. a second elongated arm with a second clamping surface substantially opposed to the first clamping surface; and c. a squeeze handle operably connected to the first clamping surface and the second clamping surface such that movement of the handle causes the first clamping surface to move toward the second clamping surface and provide the clamping force, and wherein the connection of the handle to the first clamping surface and the second clamping surface is releasable such that the handle may be disconnected from both the first clamping surface and the second clamping surface while the first clamping surface and second clamping surface provide the clamping force.

2. The bone clamp of claim 1 wherein the handle comprises a first handle portion and a second handle portion, and movement of the first handle portion toward the second handle portion is operable to move the first clamping surface toward the second clamping surface.

3. The bone clamp of claim 1 further comprising a ratchet operably connected to the first clamping surface and the second clamping surface to maintain the clamping force provided by the first clamping surface and the second clamping surface.

4. The bone clamp of claim 3 wherein the ratchet comprises a pawl operable to engage a plurality of teeth.

5. The bone clamp of claim 4 further comprising a release lever operable to disengage the pawl from the plurality of teeth and thereby release the clamping force provided by the first clamping surface and the second clamping surface.

6. A bone clamp comprising: a. a first arm comprising a first clamping surface; b. a second arm comprising a second clamping surface substantially opposed to the first clamping surface; c. a first handle releasably connected to the second arm; and d. a second handle pivotably joined to the first handle, to form a squeeze handle, the second handle operable to move toward the first handle, wherein movement of the second handle toward the first handle causes the first clamping surface to move toward the second clamping surface, and wherein release of the first handle from the second arm also results in release of the second handle from the second arm, and wherein the connection of the handle to the first clamping surface and the second clamping surface is releasable such that the handle may be disconnected from both the first clamping surface and the second clamping surface while the first clamping surface and second clamping surface provide the clamping force.

7. The bone clamp of claim 6 wherein the second handle comprises a tail and movement of the second handle toward the first handle causes the tail to forcibly engage the first arm and move the first clamping surface toward the second clamping surface.

8. The bone clamp of claim 6 wherein a plurality of teeth are provided on the second arm and a pawl is provided on the first arm, the pawl including a tip for engaging the plurality of teeth in a ratchet arrangement.

9. The bone clamp of claim 8 further comprising a release lever pivotably connected to the first arm, the release lever arranged in contact with the pawl such that pivoting movement of the release lever causes the pawl to disengage the plurality of teeth.

10. The bone clamp of claim 6 wherein the second arm includes at least one track arranged and disposed along the length of the second arm, and the first arm includes at least one runner engaging the at least one track.

11. The bone clamp of claim 10 wherein movement of the first arm toward the second arm causes the first arm to slide along the second arm with the at least one runner of the first arm in the at least one track of the second arm.

12. The bone clamp of claim 6 wherein the second arm comprises a distal end and a proximal end, the second clamping surface arranged on the distal end of the second arm and a shoulder arranged on the proximal end of the second arm.

13. The bone clamp of claim 12 wherein the first handle comprises a head with an open chamber, and the shoulder on the second arm is positioned within the channel.

14. The bone clamp of claim 13 further comprising a pin extending through the head of the first handle and through the shoulder of the second arm, thereby securing the first handle to the second arm.

15. The bone clamp of claim 14 wherein rotation of the pin allows the second arm to be released from the first handle.

16. A bone clamp comprising: a. a first elongated arm including a proximal end and a distal end with a first clamp member positioned on the distal end; b. a second elongated arm including a proximal end and a distal end with a second clamp member positioned on the distal end, the second elongated arm positioned substantially parallel to the first elongated arm and in contact with the first elongated arm; c. a squeeze handle comprising a forward handle portion connected to a rear handle portion, wherein movement of the forward handle portion toward the rear handle portion is operable to slide the first elongated arm along the second elongated arm in a first direction that causes the first clamp member to move toward the second clamp member; d. a ratchet arranged and disposed upon the first elongated arm and the second elongated arm, the ratchet comprising teeth and a pawl such that engagement of the pawl with the teeth permits motion of the first elongated arm relative to the second elongated arm in the first direction but prevents motion of the first elongated arm relative to the second elongated arm in an opposite direction.

17. The bone clamp of claim 16 further comprising a release lever in contact with the pawl wherein the release lever is operable to disengage the pawl from the teeth.

18. The bone clamp of claim 16 further comprising a tail attached to the forward handle portion, wherein the tail is operable to forcibly engage the first elongated arm and move the first elongated arm in the first direction relative to the second elongated arm when the forward handle portion is moved toward the rear handle portion.

19. The bone clamp of claim 16 wherein the rear handle portion is removeably connected to the proximal end of the second elongated arm.

20. The bone clamp of claim 19 wherein the proximal end of the second elongated arm includes a shoulder and the rear handle portion includes a head having an open chamber designed and dimensioned to receive the shoulder of the second elongated arm.

21. The bone clamp of claim 20 further comprising a release pin that extends through the head, wherein the release pin is operable to be rotated to release the second elongated arm from the rear handle portion.

22. The bone clamp of claim 16 wherein the second elongated arm comprises at least one length of track, and the first elongated arm comprises at least one runner designed and dimensioned to ride in the at least one track of the second elongated arm.

23. A method for clamping a bone compression plate to a bone comprising: a. providing a bone clamp comprising i. a first arm comprising a first clamping surface; ii. a second arm comprising a second clamping surface; iii. a handle comprising a first handle portion operable to move relative to a second handle portion and cause the first clamping surface to move toward the second clamping surface; and b. placing the bone compression plate against the bone; c. placing the bone and bone compression plate between the first clamping surface and second clamping surface; d. moving the first handle portion relative to the second handle portion to cause the first clamping surface to move toward the second clamping surface and clamp the bone compression plate against the bone; and e. removing the handle from the first arm and second arm of the bone clamp, wherein the bone compression plate remains clamped against the bone after the removing step.

24. The method of claim 23 wherein the step of removing the handle from the first arm and second arm of the bone clamp comprises rotation of a release pin that secures the handle to the first arm or second arm of the bone clamp, and wherein rotation of the release pin allows the handle to be released from the first arm or the second arm of the bone clamp.

25. The method of claim 23 wherein the bone clamp further comprises a third arm comprising a third clamping surface that is different in shape than the second clamping surface, the method further comprising the step of reattaching the handle to the first arm and the third arm of the bone clamp.

* * * * *